(12) United States Patent
Kanhye

(10) Patent No.: US 10,370,695 B2
(45) Date of Patent: Aug. 6, 2019

(54) METHOD AND APPARATUS FOR PATHOGEN TESTING

(71) Applicant: Yogesh Kumar Kanhye, London (GB)

(72) Inventor: Yogesh Kumar Kanhye, London (GB)

( * ) Notice: Subject to any disclaimer, the term of this patent is extended or adjusted under 35 U.S.C. 154(b) by 0 days.

(21) Appl. No.: 15/259,808

(22) Filed: Sep. 8, 2016

(65) Prior Publication Data
US 2017/0073722 A1    Mar. 16, 2017

(30) Foreign Application Priority Data

Sep. 11, 2015 (GB) ................................. 1516129.2

(51) Int. Cl.
*G01N 21/00* (2006.01)
*C12Q 1/04* (2006.01)
*G01N 21/64* (2006.01)

(52) U.S. Cl.
CPC .......... *C12Q 1/04* (2013.01); *G01N 21/6428* (2013.01); *G01N 2021/6421* (2013.01); *G01N 2333/195* (2013.01)

(58) Field of Classification Search
CPC ....................................................... C12Q 1/04
USPC ....................................................... 436/172
See application file for complete search history.

(56) References Cited

U.S. PATENT DOCUMENTS

| 5,900,067 A | * | 5/1999 | Jones ................. G01N 21/6447 134/1 |
| 6,426,701 B1 | * | 7/2002 | Levy ....................... G08B 21/24 137/552.7 |
| 6,524,390 B1 | * | 2/2003 | Jones ...................... C09K 11/06 134/1 |
| 6,653,146 B1 | | 11/2003 | Ruvinsky et al. |

(Continued)

FOREIGN PATENT DOCUMENTS

| GB | 2458118 A1 | 9/2009 |
| WO | 2005093681 A1 | 10/2005 |
| WO | 2012022963 A1 | 2/2012 |

OTHER PUBLICATIONS

UKIPO Search Report dated Jun. 23, 2016 for GB Patent Application No. GB1516129.2, 3 pages.

(Continued)

*Primary Examiner* — Christine T Mui
*Assistant Examiner* — Emily R. Berkeley
(74) *Attorney, Agent, or Firm* — Smith IP Services, P.C.

(57) ABSTRACT

A method of testing for pathogens can include applying a pathogen indicating substance to an object, the pathogen indicating substance having one characteristic when not in contact with a pathogen and another characteristic when in contact with a pathogen, and generating a signal indicative of the level of pathogen contamination on the object by quantifying the presence of the pathogen indicating substance with the pathogen indicating characteristic on the object. An apparatus for testing for pathogens can include a (Continued)

dispenser for dispensing a pathogen indicating substance, the pathogen indicating substance having one characteristic which is altered to another characteristic on contact with a pathogen, a main sensor for detecting a level of pathogen contamination by quantifying the pathogen indicating substance having the pathogen indicating characteristic, and a control unit for generating a signal indicative of the level of pathogen contamination detected by the sensor.

24 Claims, 5 Drawing Sheets

(56) References Cited

U.S. PATENT DOCUMENTS

2012/0212344 A1* 8/2012 Forsberg ............... G08B 3/10
340/573.1
2018/0055974 A1 3/2018 Gazendam

OTHER PUBLICATIONS

GB Examination Report dated Oct. 12, 2018 for GB Patent Application No. GB1516129.2, 17 pages.

* cited by examiner

METHOD AND APPARATUS FOR PATHOGEN TESTING

CROSS-REFERENCE TO RELATED APPLICATION

This application claims the benefit under 35 USC § 1.119 of the filing date of United Kingdom patent application no. 1516129.2 filed on 11 Sep. 2015. The entire disclosure of this prior application is incorporated herein by this reference.

BACKGROUND

The present invention relates to pathogen testing, and particularly but not exclusively to systems and methods for the improvement of hand hygiene in a clinical setting.

Hands are the most common way in which microorganisms, particularly bacteria, might be transported and subsequently cause infections, especially in those who are most susceptible to infection. The healthcare setting, in particular, contains a diverse population of microorganisms and this must be considered when caring for those who are susceptible to infection. Although potentially pathogenic microorganisms can be detected in air, water and on surfaces, determining their role in infection can be difficult. It must be considered that contamination of all patient/resident/client environments will occur and must be controlled in some manner.

The transfer of microorganisms from environmental surfaces to patients is largely considered to be via direct (hand) contact with these surfaces, or the direct contact of their healthcare professionals with such surfaces and subsequent contact with the patient. As a consequence, it is widely considered that hand hygiene is paramount in reducing infection spread via this route as well as the appropriate control of the environment. Good hand hygiene is the most important practice in reducing transmission of infectious agents, including Healthcare Associated Infections (HCAI) during delivery of care. The term hand hygiene used in this document refers to the processes used to maintain the cleanliness and hygiene of the hands, including traditional hand washing using soap and water and hand decontamination achieved using other solutions, such as alcohol hand rub/gel.

It is known that hand washing with soap and water is the preferred method of maintaining hand hygiene. Although alcohol hand rub is more convenient and less time consuming than hand washing, repeated use can cause drying of the hands, which in turn results in damage to the hand surfaces, such as cracks and cuts. The damage caused can provide better locations to harbour pathogens, and thereby actually increase the risk of transmitting an infection to a patient. Hand washing does not dry the hands out in this manner, so it is desirable to promote hand hygiene through hand washing.

Furthermore, traditional hand washing with soap and water actively removes harmful bacteria from hands. Hand sanitising gel renders the majority of the harmful bacteria inactive depending on how resistant the bacteria are and how thoroughly the gel is applied to the hands. However, hand-sanitising gel of this type does not remove the bacteria from the hands. It is also known that prolonged use of hand sanitising gel on bacteria can in time make harmful bacteria develop/evolve to become more resistant to the sanitiser and thus more harmful to people. Therefore, it is desirable to promote hand washing over the use of hand sanitising gels.

Various systems and methods for maintaining hand hygiene have been created previously. In particular, the systems disclosed in publications US2009265990A1, WO2014027030A2, GB2458118A, CA2674654A1, and US2011025509A1 are all designed to improve hygiene in a designated area, such as a room with a door. In these systems, a hand sanitiser or soap dispenser is located proximate to a door. Access through the door is prevented or discouraged until the dispenser has dispensed sanitiser. In most cases, a manual override is available in the event that urgent access is required through the door, or an alarm is sounded if the door is opened without prior activation of the dispenser.

A slightly different type of system is disclosed in publications US 2014139339A1 and CA 2807337A1. In these systems, a dispenser is located inside a location where hand hygiene must be maintained, such as a patient's room. The dispenser detects the entry of a person into the room and, if the dispenser is not activated within a predetermined time period from entry, then an alarm is sounded until the dispenser is activated.

However, a common flaw with the abovementioned systems is that there is a presumption that the hand hygiene routine (i.e. hand washing or alcohol hand rubbing) was performed correctly after activation of the dispenser. Therefore, it is relatively easy for these systems to be circumvented (e.g. by activating the dispenser, but not actually performing the hand wash or alcohol rub).

It is apparent then that improvements in the field of hand hygiene are necessary to provide more robust and reliable systems. It is an object of the present invention to provide such an improvement.

STATEMENT OF INVENTION

In a first aspect, the present invention provides a method of testing for pathogens comprising: applying a pathogen indicating substance to an object, the pathogen indicating substance having a first characteristic when not in contact with a pathogen and a second characteristic when in contact with a pathogen; and generating a signal indicative of the level of pathogen contamination on the object by quantifying the presence of pathogen indicating substance with the second characteristic on the object.

The method of the present invention provides a signal indicative of the level of pathogen contamination on the object, thereby providing an indication of the level of contamination of that object. The signal can be used to simply provide information, to control an auxiliary device or process, or in a feedback loop to improve cleanliness.

The pathogen indicating substance in itself may not remove or destroy pathogens.

Applying the pathogen indicating substance may comprise dispensing the substance onto the object directly, or onto an intermediate surface to be transferred to the object. The applying step may also comprise distributing the substance across the surface of the object, preferably over the entire surface of the object.

The pathogen indicating substance is any substance which has a first characteristic when not in contact with a pathogen and a second characteristic when in contact with a pathogen, thereby indicating the presence of a pathogen in contact with the substance. It should be understood that contact with the pathogen includes contact with the pathogen itself, contact with a product, for example a waste product, of the pathogen or contact with a component part of the pathogen, for example DNA or RNA, The first characteristic may change into the second characteristic on pathogen contact and both first and second characteristics may be measurable by the same sensing apparatus. The second characteristic may be an enhanced version of the first characteristic, for example enhanced luminescence or fluorescence when the substance is in contact with the pathogen. The change in characteristic and/or the presence of the second characteristic and/or reduction in the first characteristic from an expected level should be measurable to thereby allow identification of the presence of one or more pathogens. Preferably, the first and second characteristics are optical characteristics. More preferably, the original or first characteristic is a first type of fluorescence, non-fluorescence, luminance, or non-luminance, and the altered or second characteristic is a second type of, or enhanced, fluorescence, non-fluorescence, luminance or non-luminance. Yet more preferably, the first characteristic is fluorescence in a first colour, or wavelength, under ultraviolet light, and the second characteristic is fluorescence in a second colour, or wavelength, or enhanced fluorescence at substantially the same wavelength, under ultraviolet light.

Alternatively, the first and second characteristics may be colour characteristics, thermal characteristics, texture characteristics, reflective, refractive, or opacity characteristics.

Preferably, the pathogen indicating substance is a gel or liquid. More preferably, the substance comprises one or more of Poly(N-isopropylacrylamide) (PNIPAm), an antibiotic (preferably vancomycin), and a fluorescent dye (preferably ethidium bromide).

Pathogens in the context of the present application are undesirable contaminants which can jeopardise hygiene and promote or cause disease. Pathogens may include bacteria, viruses, fungi or their spores, parasites, prions, viroids, or any other infectious agent that may cause disease. More preferably, the pathogens may be gram negative bacteria and/or gram positive bacteria. Even if the pathogen indicating substance characteristics are altered in response to only a limited type of pathogen, for example gram negative and/or gram positive bacteria, the present invention may still provide an general test for all types of pathogen, as if one type of pathogen has been eliminated from the object, for example by cleaning the object, then it is most likely that other types of pathogen have been eliminated too.

The quantifying step may comprise any process which can be utilised to detect, and thereby quantify the second characteristic of the pathogen indicating substance. As the substance only exhibits the second characteristic upon contact with a pathogen, the identification of substance having the second characteristic confirms the presence of at least one pathogen at a level sufficient to cause a detectable change in the indicating substance. As pathogens are typically microscopic, the quantifying step may not identify individual pathogens, but may quantify simply the presence or absence of close-knit groups, or colonies, of pathogens, or the distribution of pathogens on the object. In other examples, the quantifying step may quantify individual pathogens, and also provide an indication of the total level of pathogens identified.

In the signal generating step, a signal is generated, preferably automatically, which is indicative of the level of pathogen contamination quantified on the object during the quantifying step. The level of pathogen contamination in the present application should not be limited to a simple count of the actual number of pathogens identified, but should also be understood to encompass a number of groups of identified pathogens, a distribution of pathogens or groups thereof, percentage of surface coverage, degree of contamination, or a concentration of pathogens or groups thereof. Therefore, it should be clear to the skilled person that the term level of pathogens may also be a relative or general term. For example, a high level of pathogen contamination should be understood to mean an unacceptable amount, concentration, or distribution of pathogens, or a level of pathogen contamination above a predetermined threshold, whereas a low level of pathogen contamination should be understood to mean an acceptable amount, concentration, and/or distribution of pathogens, or a level of pathogen contamination below a predetermined threshold.

The predetermined threshold may be a level of pathogen contamination considered to be unacceptable to be present on the object being measured. The threshold may be a risk based determination of a percentage chance of infection. The predetermined threshold may be specified or dependent upon the object being tested, the location of the object, or the hygiene standards required.

An unacceptable level of pathogen contamination or a level of pathogen contamination above the predetermined threshold may an amount, concentration, or distribution of pathogens that is not deemed to represent a high risk of disease transmission, while an acceptable level of pathogen contamination or a level of pathogen contamination below the predetermined threshold should be understood to mean an amount, concentration, or distribution of pathogens that is deemed to represent a higher risk of disease transmission.

Furthermore, if it is stated that no pathogens are present, the skilled person should also understand that in reality it may be impossible to have a complete absence of pathogens, and thus that no pathogens will be analogous with a negligible, acceptable, or safe level of pathogen contamination.

The generating step may comprise automatically generating a signal having a first type when a level of pathogen contamination greater than the predetermined threshold is quantified, or generating a signal having a second type when less than the predetermined threshold of pathogen contamination is quantified.

The signal generated may be a digital signal or an analogue signal. Preferably, the signal may be a binary signal, which may take a high value or a low value. The signal generated may have a high value when the level of pathogen contamination quantified in the quantifying step is equal to or more than the predetermined threshold, and the signal generated may have a low value when the level of pathogen contamination quantified in the quantifying step is less than the predetermined threshold.

The signal generated may also have a third possible type. The third type may be a 'no determination possible' signal, which is generated in the instance that it is not possible to quantify the level of pathogen contamination and may indicate that a retest is required.

Alternatively, the signal may have a discreet or continuous range of values indicative of the level of pathogen contamination. High levels of pathogen contamination being quantified may result in generation of high signals, while low levels of pathogen contamination being quantified may result in the generation of low value signals, or vice versa.

Preferably, the object may be one or more human hands. Hands are the most common route of transmission of pathogens, so the method may further comprise the initial step of identifying the object as one or more human hands. This may result in the dispensing step only be performed if the object is identified as one or more human hands. Preferably, the applying step further comprises detecting the presence of an object, and dispensing the pathogen indicating substance onto the object. As noted above, the step of identifying that object may take place between the detecting and dispensing step and may prevent the dispensing step if the identification of the object does not successfully identify an appropriate object.

Preferably, the quantifying step comprises using at least one optical sensor. The quantifying step may further comprise capturing one or more images of the object, and more preferably comprise digitally analysing the one or more images to provide a quantitative indication of the amount of the second characteristic of the pathogen indicating substance quantified and thereby determine the level of pathogen contamination present on the object. Suitable techniques for digital analysis are known in the art and may involve image processing using a processor, for example a graphics processor. Digitally analysing the one or more images may comprise identifying pathogen indicating substance having the second characteristic in the images. The quantifying step may also comprise illuminating the object with ultraviolet light. The images may be captured by a camera or an ultraviolet light sensitive camera.

Quantifying the presence of pathogen indicating substance with the second characteristic on the object may comprise, for example, comparing an area occupied by an image of the object and an area of the image occupied by pathogen indicating substance with the second characteristic to provide a quantitative measure of the percentage of the surface of the object which is contaminated by a pathogen. A processor could be used to automatically conduct some or all of these steps using image processing software and/or appropriate algorithms. The skilled person will be able to conceive various other methods for conducting the quantifying step.

Preferably, the method further comprises communicating the signal to an auxiliary device. The auxiliary device may be a computer server, a database, a control system for a device, or an actuable device. The signal may be recorded in a database. The method may further comprise identifying a user of the device and recording the signal in a database of the user's previously generated signals.

Preferably, the method further comprises the step of actuating an auxiliary device based upon the signal.

The method may be a method is a method of accessing a door, and the auxiliary device may be a locking device for selectively locking a door. The method may also comprise unlocking the locking device if the signal generated is of the second type.

The method may further comprise selectively preventing, or permitting access to a location dependent upon the signal. Selectively preventing access to a location may comprise locking a locking device, and/ or activating or maintaining an alarm system, or closing a door or other barrier. Selectively permitting access to a location may comprise unlocking a locking device, opening a door or other barrier, and/or deactivating an alarm system.

The location may be a room, a cupboard, a building, or, more generally, the other side of a barrier. The location may be a patient room or a hospital ward, in which case the barrier is a door.

The method may further comprise displaying a visual indication of the signal generated in the generating step.

Preferably the method further comprises the steps of detecting the presence of a user, and/or outputting a reminder, preferably an audio and/or visual reminder, to the user to test their hands for pathogens or to perform one, many, or all steps of the method. Reminders may be outputted for example to remind the user to: apply pathogen detecting substance to the object, place object under the optical sensor, to turn over the hands to present a different side of the object to the optical sensor or to open the door. Different reminders may be outputted dependent upon whether a positive or negative signal is generated, for example if a negative signal is generated, the reminder may indicate to the user comprising instructions on how to avoid generation of a negative signal in a future performance of the method. If a positive signal is generated, the reminder could remind the user to wash the pathogen indicating substance off their hands before continuing.

In a further aspect, the present invention provides an apparatus for testing for pathogens comprising: a dispenser for dispensing a pathogen indicating substance, the pathogen indicating substance having a first characteristic which is altered to a second characteristic on contact with a pathogen; a main sensor for detecting a level of pathogen contamination by quantifying pathogen indicating substance having the second characteristic; and a control unit for generating a signal indicative of the level of pathogen contamination detected by the sensor.

The apparatus or system may further comprise a user sensor for detecting the presence of a user near the apparatus or system, and an output for outputting a reminder, preferably an audio and/or visual reminder, when a user is detected by the user sensor.

Further preferable features are recited in the appended dependent apparatus claims.

The present invention may also provide an apparatus suitable for use in any of the methods described herein.

In a further aspect, the present invention also provides a system for door access comprising any of the apparatuses described herein.

It will be understood by the skilled person that these preferable and advantageous features may be combined with one another and that any resulting embodiments will also be embodiments of the invention.

DETAILED DESCRIPTION OF THE EMBODIMENT

A better understanding of the present invention will be obtained from the following detailed description. The description is given by way of example only and makes reference to the accompanying drawings, in which.

Figure 1:
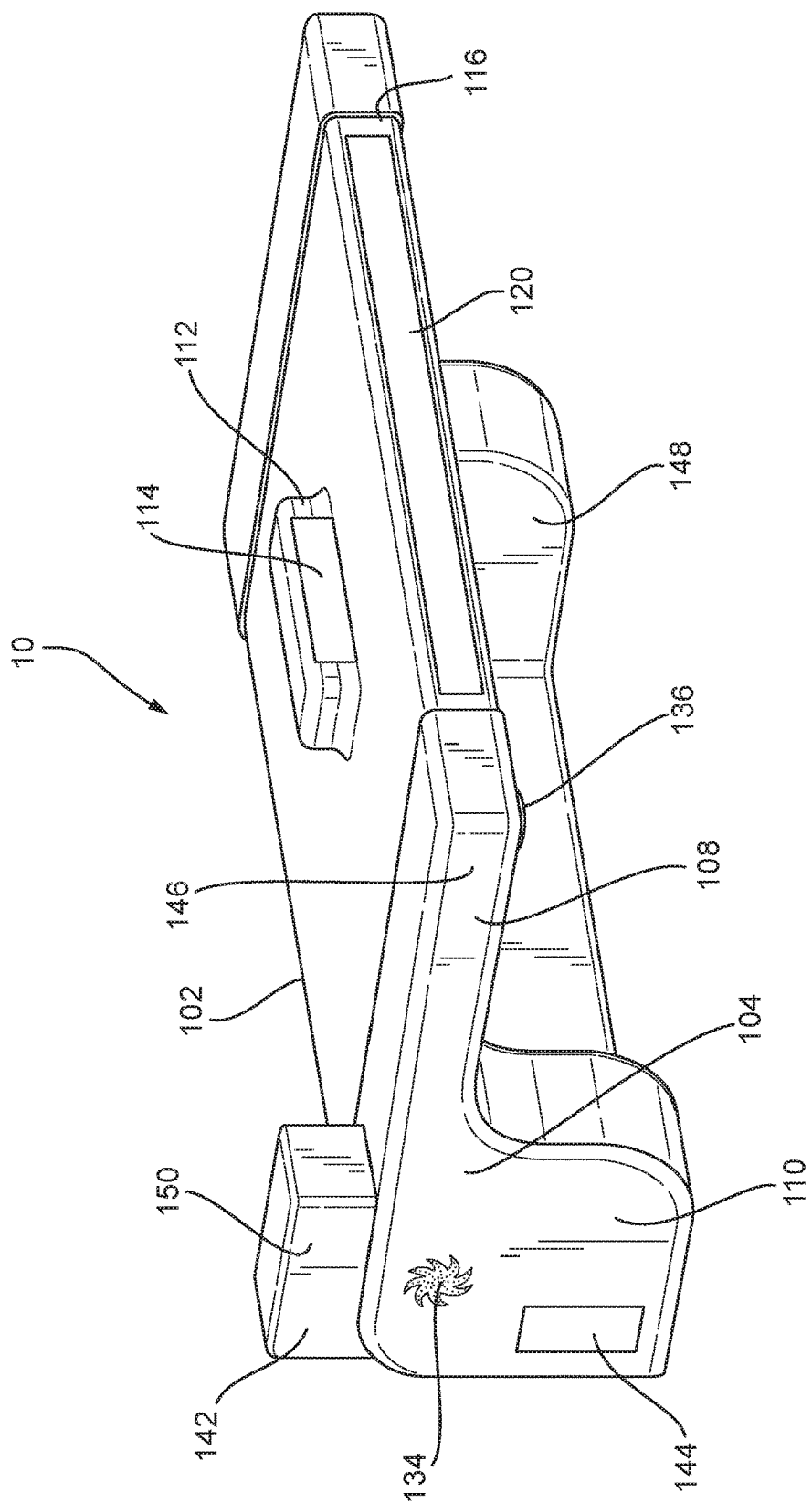
FIG. 1 is a perspective view of a pathogen testing apparatus according to the present invention.
Figure 2:
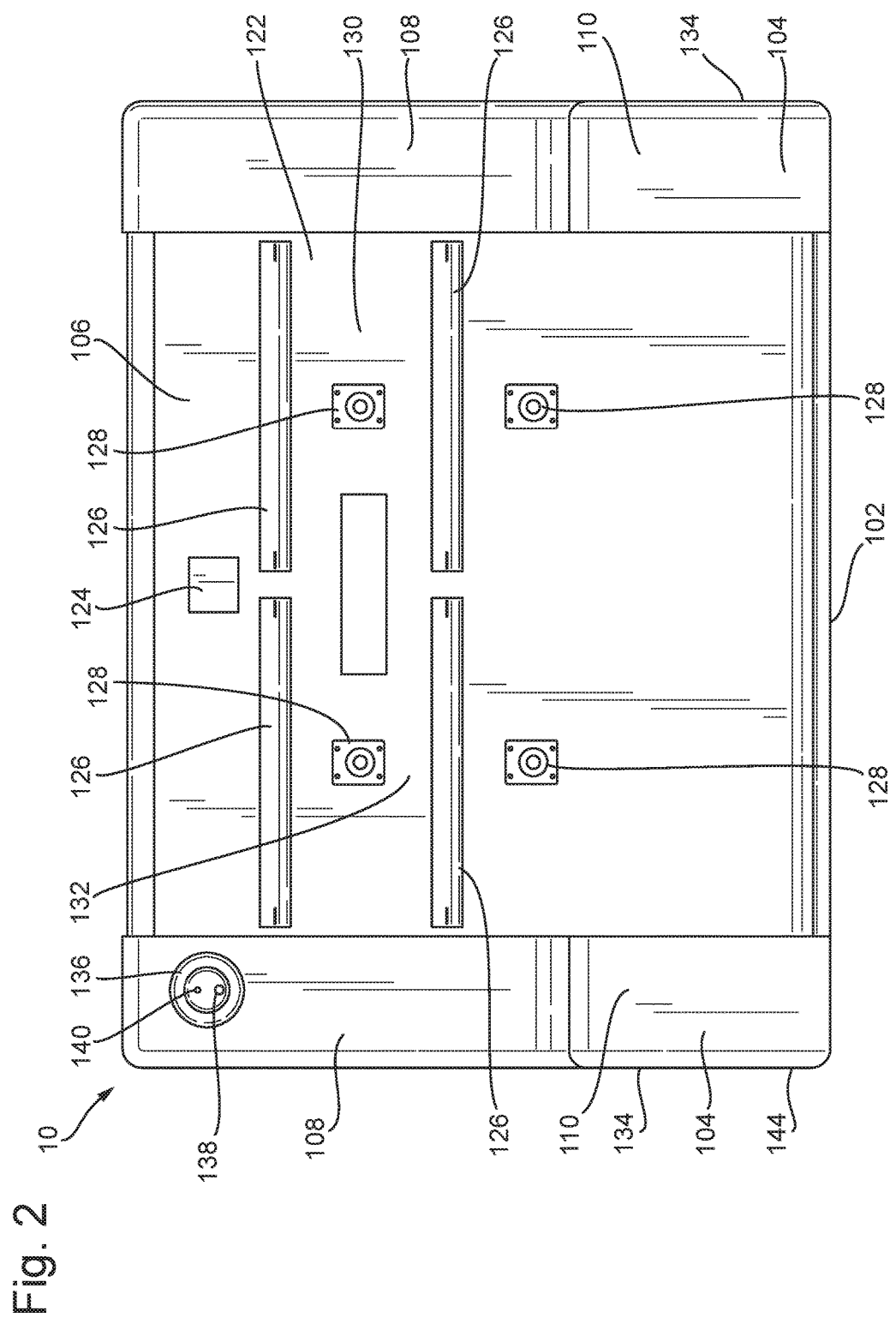
FIG. 2 shows a bottom view of the pathogen testing apparatus of FIG. 1.

Turning to FIGS. 1 and 2, a pathogen testing apparatus 10 is shown. The apparatus 10 is connectable to a vertical surface, such as a wall (not shown) on its rear surface 102 by commonly known attachment means, such as screws, nails, bolts, or adhesive.

The apparatus 10 comprises two side portions 104 with a central portion 106 spanning therebetween. The side portions 104 comprise a cantilever portion 108 ultimate from the rear surface 102, and a base portion 110 proximate to the rear surface 102. The base portions 110 are substantially deeper than the cantilever portions 108, such that the apparatus is substantially a shelf-like having a roughly L-shaped cross section.

The base portion 110 of the left side portion 104 (when viewed from the front) houses a speaker 134, a substantially transparent polymer gel reservoir 142, and a transparent viewing window 144. The cantilever portion 108 of the left side portion 104 houses a polymer gel dispenser 136 comprising a dispenser sensor 138 and a dispenser nozzle 140 the dispenser. The cantilever portion 108 also comprises an LED indicator 146 for indicating the power of the machine and the fill level of the reservoir 142. The base portion 110 of the right side portion 104 houses a second speaker 134 and a CPU 148 control unit for operating the apparatus, which is connected to the sensors, lights, camera, LEDs, speakers, and dispenser described herein.

The central portion 106 of the apparatus 10 has a vertical protrusion 112 on its upper surface which houses a front-facing motion sensor 114. The front surface 116 of the central portion 106 is substantially covered by a strip LED array 120. The underside of the central portion 106 is vertically recessed from the side portions 104 to create a substantially flat horizontal sensor surface 122 facing downwards.

Numerous components of the apparatus are located on the sensor surface 122. A downward-facing hand motion sensor 124 is provided proximate a front edge of the surface 122. A four ultraviolet (UV) strip lights 126 are arranged in two lines on the surface 122 rearward of the hand sensor 124, each line spanning substantially the entire width of the surface 122. The two lines formed are spaced apart. Also provided on the sensor surface 122 are four downward-facing cameras 128. A first two of the cameras 128 are provided between the two lines of UV lights 126, each located halfway across each half of the width of the surface 122. A second two of the cameras 128 are provided rearwards of the second line of UV lights 126, located at the same widths across the surface 122 as the first pair of cameras.

The pair of cameras 128 and UV lights 126 on the right-hand side of the surface (when viewed from the front) form a right sensor array 130, and the pair of cameras 128 and UV lights 126 on the left-hand side of the surface (when viewed from the front) form a left sensor array 132.

Providing two cameras 128 for each hand allows the hands to be captured from different perspectives, thereby allowing more views of the hands to be analysed and increasing the accuracy of the detection of pathogens. In addition, the provision of two cameras for each hand enables larger hand sizes to be captured more easily. In this way, the apparatus 10 can operate effectively to capture images of a large range of hand sizes above and below the average hand size thus enabling accurate usage by the majority of the population of potential users.

Figure 3:
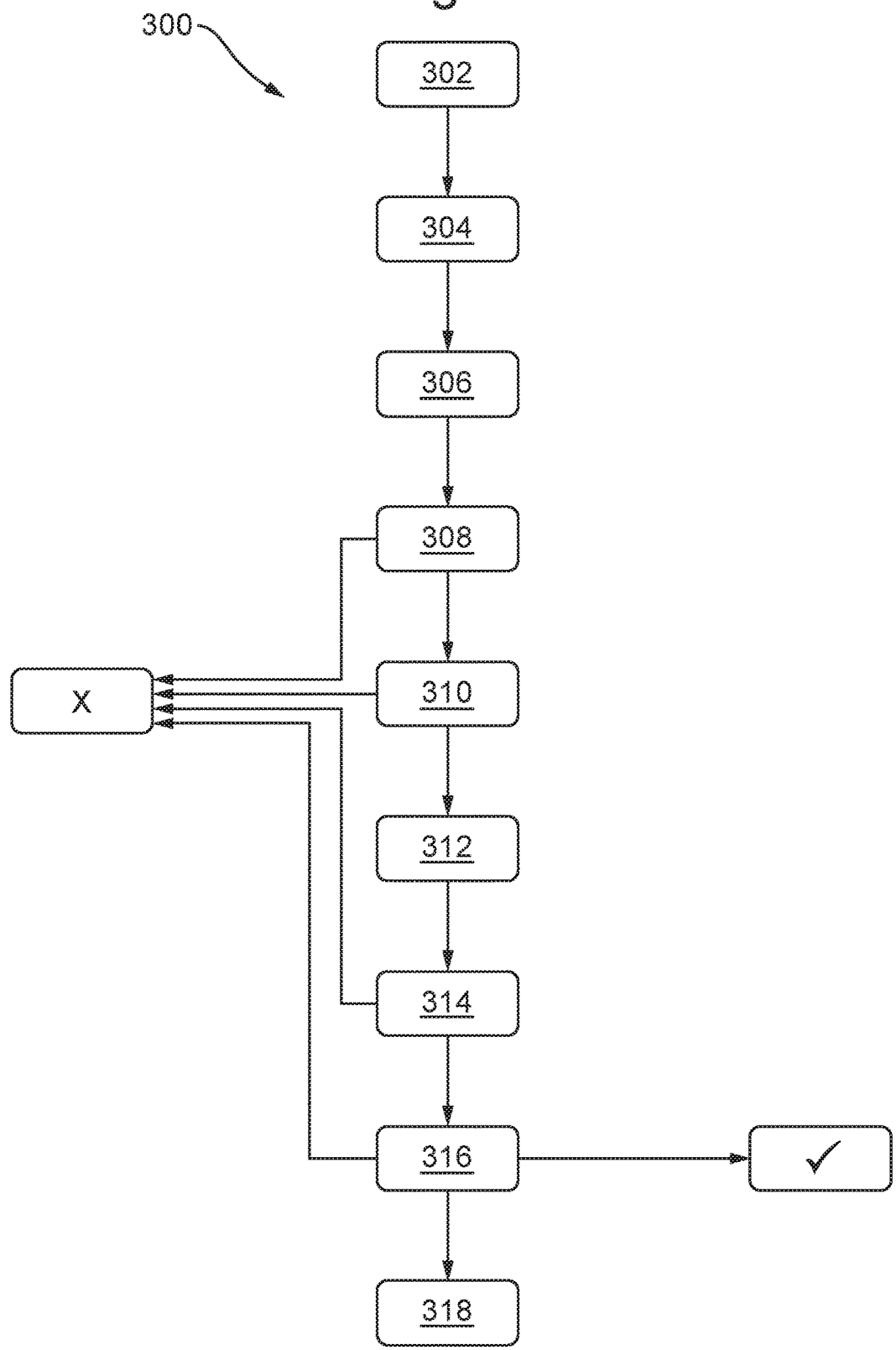
FIG. 3 shows a representation of a method of testing for pathogens according to the present invention.

A method 300 of use of the apparatus 10 will now be described with reference to FIG. 3. In a first step 302, the dispenser sensor 138 is activated by the CPU 148 and an object, in this case a user's hands, is located below the dispenser 136.

In step 304, the sensor 138 detects the presence of the hands and submits this information to the CPU 148, which in turn transmits a signal to the dispenser 136 to dispense a predetermined amount of polymer gel 150 onto the hands. The user then distributes the polymer gel 150 across the entirety of the hands' surfaces.

In the next step 306, the hands are moved beneath the sensor surface 122. The motion sensor 124 senses the presence of the hands and the CPU 148 consequently switches on the UV lights 126 to illuminate the hands and also switches on the cameras 128. The hands are located such that the back surface of the right hand is located below the right sensor array 130 and the back surface of the left hand is located beneath the left sensor array 132.

In immediately subsequent step 308, the UV lights 126 remain switched on to illuminate the hands, which are covered with the polymer gel 150. Under UV light, any gel that has not been in contact with gram-negative bacteria fluoresces in a first colour, or at a first intensity, and any polymer gel that has been in contact with gram-negative bacteria fluoresces in a second colour, or at a second intensity. The cameras 128 of the right sensor array 130 capture images and/or video of the back of the right hand, and the cameras 128 of the left sensor array 132 capture images and/or video of the back of the left hand. The images/video of both hands is relayed to the CPU 148.

The CPU 148 first assesses whether two hands can be identified in the respective images using appropriate image processing software and/or algorithms. The CPU 148 assesses whether the objects are hands by first identifying the outline of the hand and comparing to known hand shapes to identify the object positively as a left/right hand as appropriate for the left/right sensor arrays respectively. If the objects are not positively identified as hands due to their shape, the CPU 148 will generate a negative signal, which can be indicated externally by illuminating the LED array 114 in a red colour. The CPU may also indicate via speakers 134 that this is the reason that a negative signal has been generated. If the objects are identified positively as hands, then the CPU 148 then moves on to assessing whether the entire area of the hand is covered in gel.

As the hands must be entirely coated with polymer gel 150 in order for the pathogen testing method to be effective, the CPU 148 assesses using image processing whether the entire area within the hand outline is fluorescing in either the first or the second colour. If the CPU 148 does not detect that the entirety of both hands are fluorescing in wither the first or second colour, then the CPU generates a negative signal, and indicates by LED array 114 and also via speakers 134 the reason that a negative signal has been generated. If the hands are detected to be entirely covered in polymer gel 150, then the CPU can move onto assessing whether gram negative bacteria are present on the hands.

In step 310, pathogens, in particular gram negative bacteria, are quantified. The CPU 148, using the images captured in step 308 above, assesses whether any polymer gel 150 which is fluorescing in the second colour is present on the hands. This step can be performed by assessing the entirety of the image, or in a pixel-by-pixel analysis of the pixel colour or intensity. If any polymer gel 150 fluorescing in the second colour, or with enhanced intensity, is identified in the images/video of the hands, then a negative signal is generated by CPU 148, and an indication of the reason for the generation of the negative signal communicated by speakers 134 and LED array 114. If no polymer gel fluorescing in the second colour, or with enhanced intensity, can be identified, or is identified at a level below a predetermined threshold, then a positive signal is generated by the CPU 148, which is communicated to the user by illuminating the LED array 114 green. The CPU 148 then instructs the user to turn the hands over so that the palm surface of the hands is facing the sensor surface 122. If a negative signal is generated by the CPU 148 in this step, then this indicates that the hands were not sufficiently sanitised to remove pathogens. Therefore, a negative signal in step 310 may be accompanied by an indication from the CPU 148 via speakers 134 to re-sanitise the hands before beginning the method 300 again at step 302.

In step 312, the user turns the hands over such that the palm surface of the right hand and right hand are located below the right sensor array 130 and left sensor array 132 respectively.

The next step 314 is that the hands are positively identified as human hands, and the gel coverage of the hands is confirmed in a similar manner as performed in step 308 above. The CPU 148 may also assess whether the hands are the same as those assessed in step 308, by comparing the shapes of the hands in the images collected in the present step and step 308. Furthermore, it may be assessed whether the hands have in fact been turned over, for example by analysing the location of the thumbs, the texture of the palms, identifying palm or fingerprint patterns or otherwise.

In step 316, pathogens on the palm surface of the hands are identified in the same manner as in step 310. If pathogens are identified, then a negative signal is generated and indicated to the user. However, if no pathogens are identified, or are identified at a level below a predetermined threshold, then a positive signal in generated and communicated to the user by again indicating a green light with LED array 114. To reach step 316, a positive signal must have been generated in 310, indicating no pathogens, or pathogens at a level below a predetermined threshold, on the back surface of the hands. Therefore, if a positive signal is also generated in step 316, indicating that no pathogens were indicated on the palm surfaces of the hands, then it can be considered that the hands are free of pathogens, or that any contamination is below a predetermined threshold level.

In optional step 318, if a positive signal was generated by the CPU 148 in step 316, then this signal is communicated to an auxiliary device or process to inform that device or process that pathogens were not indicated on the object. If a negative signal is generated during any of the steps of method 300, then this negative signal can be communicated to the auxiliary device to inform another process or apparatus that pathogens were indicated on the object.

It should be understood that although the above method is applied with the object being a pair of hands, the method 300 could also be applied to any type of object which requires testing for pathogens. The steps 312-316 can be further repeated on other sides of a many-sided object to be tested if it is of interest to identify pathogens on more than two sides.

Figure 4:
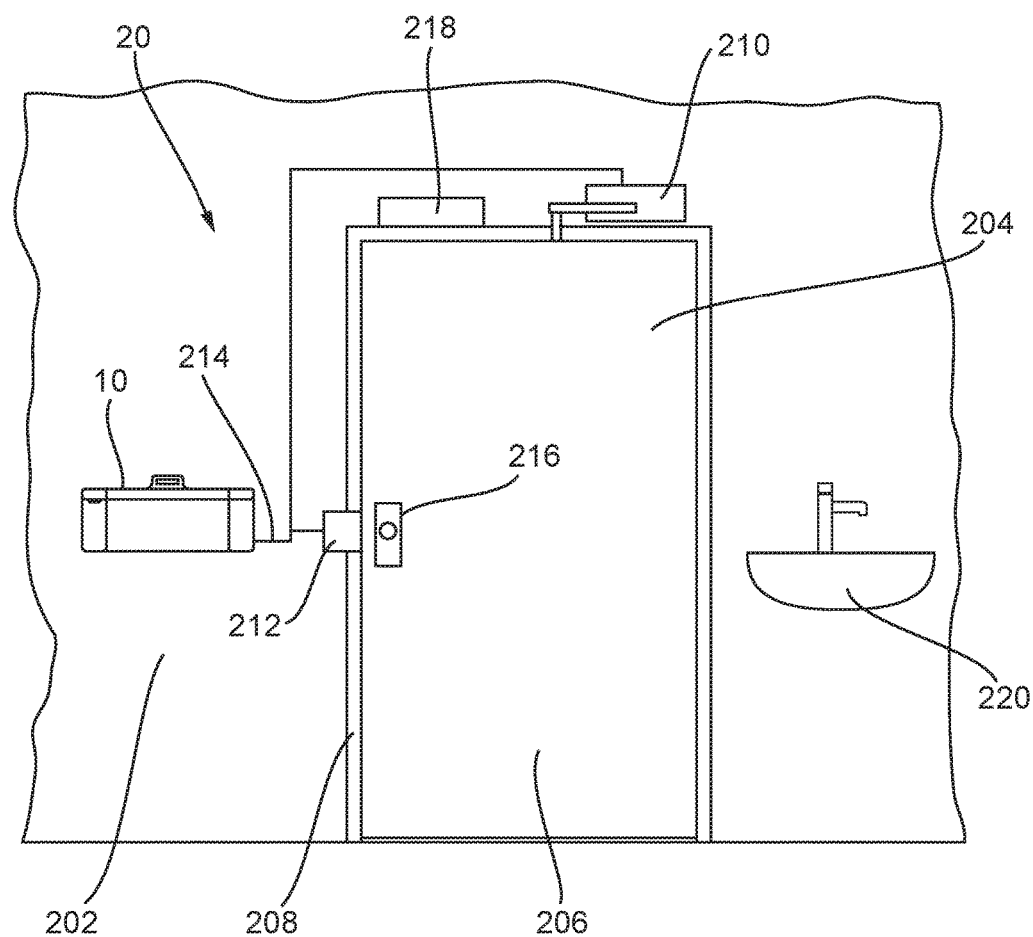
FIG. 4 shows a door access system according to the present invention.

Turning now to FIG. 4, a door access system is representatively shown. The door access system 20 comprises the apparatus 10 described above attached to a wall 202 having a door 204. The apparatus 10 is attached to the wall 202 at an appropriate height for an adult user to easily locate their hands under the sensor surface 122 of the apparatus 10 when in a standing position.

The door 204 comprises a door leaf 206 hingedly connected in a door frame 208. An automatic door opener 210 is provided for automatically opening the door to provide access for a user to a location behind the door 204. The location behind the door may be any location, but the present system is particularly useful for applications where high level hygiene/infection protection is required. For example, the door 204 may provide access to a hospital environment, such as a patient room, ward, operating theatre, laboratory, or quarantine room. The system 20 can also be used in any environment that either handles/processes food or area that requires a high level of hygiene/infection protection, such as cruise ships, restaurants, food factories, aircraft, seagoing vessels, manufacturing facilities, or research laboratories.

The system 20 further comprises a locking device 212 for locking the door 204 to prevent access to the location behind the door 204. The apparatus 10, more particularly the CPU control unit 148 is in communication with the door opener 210 and the locking device 212 via a line 214. A manual override device 216 is provided to allow the door 204 to be opened manually, thereby overriding the commands of the CPU unit 148 to the locking device 212 and door opener 210.

An alarm system 218 is provided which emits an audible and visual alarm warning when the door is opened using the manual override device 216. The alarm system 218 may be in communication with another system such as telecommunication device or devices, such as pagers or mobile devices to provide further warnings that the door 204 has been opened using the manual override device 216. Therefore, if an emergency occurs behind the door 204 (for example a patient having a sudden acute episode, such as a cardiac arrest) and immediate access is required regardless of the level of hand sanitisation, then the door 204 can be manually opened, and nearby personnel notified of the emergency. Alternatively, if the manual override device 216 is operated by an unauthorised person in the absence of an emergency, then the alarm system 218 will similarly notify nearby personnel that an intrusion has occurred. In addition, the system 20 may be in communication with an external alarm system, such as an emergency or fire alarm system of a building in chich the system is located. In the event of a fire or emergency alarm, or an error or malfunction of the system 20, the system may automatically unlock the locking device 212 such that uninhibited access through the door 204 is permitted.

A hand sanitising facility 220 is provided in the immediate vicinity of the door 204 and the apparatus 10 for sanitising the hands of a potential user of the system 20. The hand sanitising facility 220 is in this instance a traditional hand-washing basin with water and soap, but may alternatively be any other known hand sanitising means, such as an alcohol gel dispenser.

Figure 5:
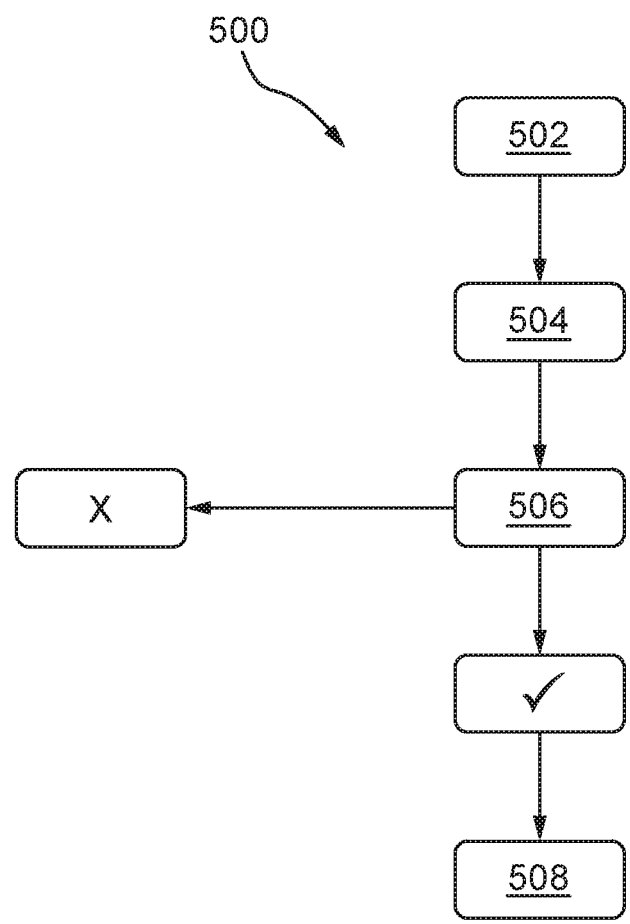
FIG. 5 shows a representation of a method of door access according to the present invention.

Referring now to FIG. 5, a method 500 of operating the system 20 is described. In the first step 502, a user wishing to access the location behind the door 204 approaches the door 204. The motion sensor 114 senses the approach of the user and sends an indication to the CPU 148.

In the next step, 504, the CPU 148 receives the information from the motion sensor 114 and issues an audible indication to the user via the speakers 134 that the user should locate their hands below the dispenser 136.

Following the audible indication, in the next step 506, the user locates their hands below the dispenser 136 and the steps recited in method 300 above are performed. The optional step 318 of this method is performed, and, in the case that a positive signal is generated in step 316, the positive signal is sent to the locking device 212 to unlock the door 204, and also to the door opener 210 to open the door without the user needing to touch the door 204, both of which are performed in step 508.

Once it has been sensed by a further sensor (not shown) that the user has entered the now open door 204 or alternatively after a predetermined time allotted to allow the user to enter the door 204, the door opener 210 then closes the door to prevent unauthorised access by a person not having performed the method 500.

If alternatively a negative signal is generated at any point in the method 300 performed during step 506, then the appropriate indication is issued by the apparatus 10. If a negative signal is generated in step 310 or 316, then the hand sanitising facility 220 is located nearby to allow the user to re-sanitise their hands to thereby restart method 500 and attempt to gain a positive signal in step 506 to thereby open the door.

The apparatus 10 may provide a voice or audio feature in relation to hand washing reminders. In any instance that the motion sensor 114 detects the presence of a person walking past the apparatus 10, the apparatus may issue a sound or voice reminder to remind the person to perform a hand hygiene operation, such as; "Please wash your hands, thank you." This function may be selectively activated or deactivated (for example at night, when the voice reminder may keep patients in a hospital ward awake) by way of a discreet on/off switch not obvious to users to the product, but known to the owners of the product and in the product manual. For example in the case of a hospital ward, the unit should be placed preferably inside the ward entrance near the entrance/exit doors to remind all visitors and staff to wash their hands upon entering the ward and before leaving the ward.

It will be understood that the apparatus 10 may not necessarily be connected to a door locking system as described above. For example, if utilised in a hospital ward, then the hand scanning functions may still be operable and can still be used by the staff to perform random hand hygiene tests and for visitors to test if their hands are clean if they so wish to do so. In this instance, the signal provided may be indicated to the user visually or audibly.

It will be understood that the apparatus, methods, and systems described herein are for exemplary purposes only, and that there are many applications compatible with the present invention. The present invention is not limited to the specific embodiments described herein. Alternative arrangements and suitable materials will be apparent to a reader skilled in the art.

The invention claimed is:

1. A method of testing a hand for at least one pathogen, the method comprising:
    applying a pathogen indicating substance to a hand, the pathogen indicating substance having a first characteristic when not in contact with the pathogen and a second characteristic when in contact with the pathogen;
    identifying an area of the hand;
    detecting whether the area of the hand is covered with the pathogen indicating substance having either the first characteristic or the second characteristic; and
    generating a signal indicative of the level of pathogen contamination on the hand by quantifying the presence of the pathogen indicating substance with the second characteristic on the hand,
    wherein the first characteristic comprises a detectable first type of fluorescence, and the second characteristic comprises a detectable second type of fluorescence, and wherein the applying, identifying, detecting and generating steps are performed after sanitising the hand.

2. The method of claim 1, wherein the quantifying comprises using an optical sensor.

3. The method of claim 1, wherein the generating comprises generating a signal having a first type when the level of pathogen contamination exceeds a first predetermined threshold, or generating a signal having a second type when the level of pathogen contamination is less than a second predetermined threshold.

4. The method of claim 1, further comprising communicating the signal to at least one of the group consisting of an auxiliary device and a process.

5. The method of claim 4, wherein the method further comprises accessing a door, and wherein the auxiliary device comprises a locking device for selectively locking the door.

6. The method of claim 5, further comprising unlocking the locking device if the signal generated is of a type indicating that the level of pathogen contamination is less that a predetermined threshold.

7. The method of claim 1, wherein the applying further comprises detecting the presence of the hand, and dispensing the pathogen indicating substance onto the hand.

8. The method of claim 1, wherein the pathogen indicating substance comprises a pathogen indicating polymer gel.

9. The method of claim 1, wherein the quantifying further comprises illuminating the hand with ultraviolet light.

10. The method of claim 1, wherein the quantifying further comprises capturing one or more images of the hand.

11. The method of claim 10, wherein the quantifying further comprises digitally analysing the one or more images, and thereby determining the level of pathogen contamination present on the hand.

12. The method of claim 1, in which an apparatus performs the applying and generating steps, the apparatus comprising:
    a dispenser for dispensing the pathogen indicating substance;
    a main sensor for detecting a level of pathogen contamination by quantifying the pathogen indicating substance having the second characteristic; and
    a control unit for generating a signal indicative of the level of pathogen contamination detected by the main sensor.

13. The method of claim 12, further comprising an auxiliary device for receiving the signal from the control unit.

14. The method of claim 12, wherein the main sensor comprises an optical sensor.

15. The method of claim 14, wherein the optical sensor comprises an image capture device, and wherein the control unit comprises a processor for image analysis.

16. The method of claim 12, further comprising an object sensor for detecting presence of an object.

17. The method of claim 16, wherein the dispenser is operably associated with the object sensor such that the pathogen indicating substance is dispensed upon detection of the object by the object sensor.

18. The method of claim 12, wherein the first characteristic comprises a first type of fluorescence, and the second characteristic comprises a second type of fluorescence.

19. The method of claim 12, wherein the pathogen indicating substance comprises a gel.

20. The method of claim 19, wherein the gel comprises one or more of Poly(N-isopropylacrylamide) (PNIPAm), an antibiotic and a fluorescent dye.

21. The method of claim 13, wherein the auxiliary device comprises a locking device for selectively locking a door.

22. The method of claim 1, wherein the pathogen comprises at least one of the group consisting of gram negative bacteria and gram positive bacteria.

23. The method of claim 1, further comprising at least one of: (a) detecting the presence of a user, and (b) outputting a reminder to the user to test the hand for the pathogen.

24. The method of claim 12, further comprising a user sensor for detecting presence of a user near the apparatus, and an output for outputting a reminder in response to the user being detected by the user sensor.

* * * * *